United States Patent [19]

Gupta

[11] Patent Number: 5,194,456
[45] Date of Patent: Mar. 16, 1993

[54] UV ABSORBERS AND PMMA MATERIAL CONTAINING SUCH ABSORBERS

[75] Inventor: Amitava Gupta, San Marino, Calif.

[73] Assignee: Ioptex Research, Inc., Irwingdale, Calif.

[21] Appl. No.: 527,019

[22] Filed: May 22, 1990

Related U.S. Application Data

[63] Continuation-in-part of Ser. No. 445,277, Dec. 4, 1989, abandoned.

[51] Int. Cl.[5] .................. C08F 232/08; C08F 120/36; C07D 249/20
[52] U.S. Cl. .................................... 523/106; 514/972; 524/94; 524/194; 548/257; 548/261
[58] Field of Search .................. 523/106; 524/94, 194; 548/257, 261; 514/972

[56] References Cited

U.S. PATENT DOCUMENTS

| | | | |
|---|---|---|---|
| 4,260,768 | 4/1981 | Lorenz et al. | 548/261 |
| 4,716,234 | 12/1987 | Dunks et al. | 548/259 |
| 4,745,194 | 5/1988 | Vogl et al. | 548/261 |

*Primary Examiner*—Paul R. Michl
*Assistant Examiner*—Andrew E. C. Merriam
*Attorney, Agent, or Firm*—Roseman & Colin

[57] ABSTRACT

The novel compound of the formula

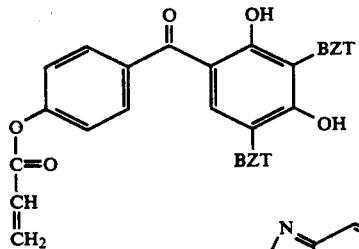

has been found to be useful as a UV absorber.

A novel PMMA material has incorporated therein a UV absorbing amount of the novel UV absorber. Intraocular lenses and contact lenses are produced from PMMA having incorporated therein a UV absorbing amount of the novel UV absorber.

Eyeglasses are produced having lenses of a polycarbonate material which has incorporated therein a UV absorbing amount of the novel UV absorbed.

6 Claims, 2 Drawing Sheets

UV ABSORBERS AND PMMA MATERIAL CONTAINING SUCH ABSORBERS

This is a continuation-in-part of my copending application Ser. No. 445,277 filed Dec. 4, 1989 now abandoned.

The present invention relates to a novel ultraviolet light absorber, to a novel polymethylmethacrylate (PMMA) material having incorporated therein a UV absorbing amount of the novel UV absorber and to intraocular lenses and contact lenses formed from said novel PMMA material and to eyeglasses formed from a polycarbonate material which contains a UV absorbing amount of the novel UV absorber.

More particularly, the novel UV absorber of the present invention is a compound of the formula (I)

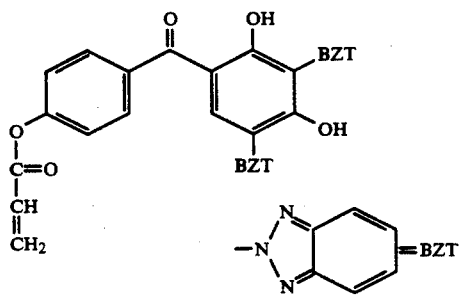

This compound is effective for absorbing UV light in the range of about 200 nm to about 450 nm particularly in the range of 240 nm to 420 nm.

The present invention also comprises a novel polymethylmethacrylate (PMMA) material of the formula (II) having incorporated therein a UV absorbing amount of the novel UV absorber of the present invention formula (I). It is believed that the novel PMMA material will be of the formula (II)

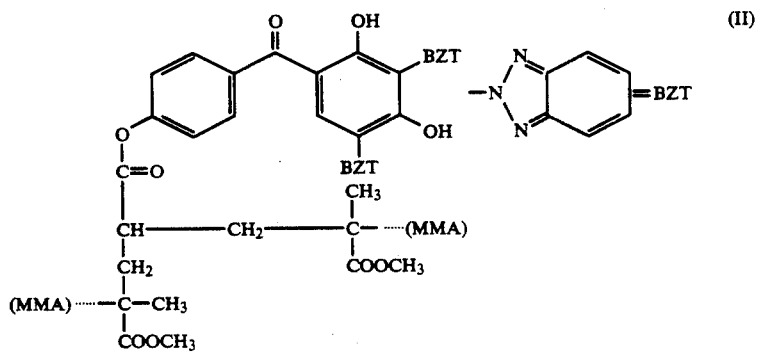 (II)

wherein MMA is the monomer unit.

Generally from about 0.1% to about 5% by weight of the novel UV absorber is incorporated in the PMMA based on the weight of that material.

According to one embodiment of the present invention from about 0.1% to about 2% by weight of the UV absorber is incorporated. About 0.15% by weight is a preferred amount.

According to a further embodiment of the present invention, an intraocular lens (IOL) is produced which comprises a novel PMMA material of the formula (II) which comprises PMMA having incorporated therein, a UV absorbing amount of the novel UV absorber of the formula (I)

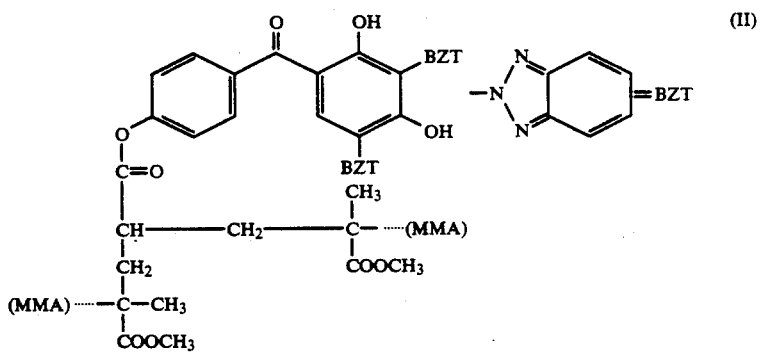 (II)

wherein MMA has the above meaning.

According to a further embodiment of the present invention, the intraocular lens comprises the novel PMMA material having from about 10 ppm to about 500 ppm of the novel UV absorber incorporated per part of PMMA. From about 100 ppm to about 250 ppm is a preferred amount.

According to a further embodiment of the present invention, a contact lens is produced which comprises a novel PMMA material of the formula (II) which comprises PMMA having incorporated therein, a UV absorbing amount of the novel UV absorber of the formula (I)

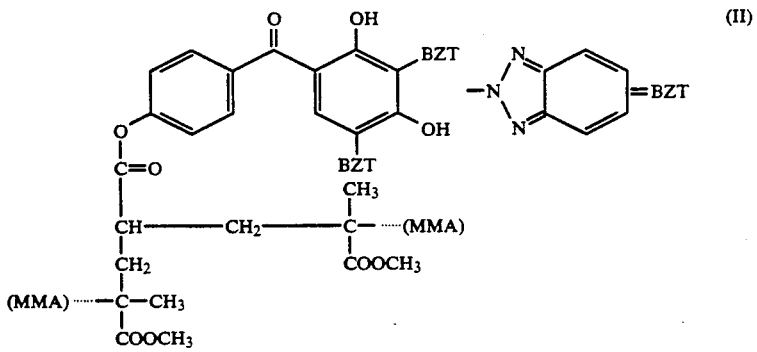

(II)

wherein MMA has the above meaning.

According to a further embodiment of the present invention, a contact lens is produced which comprises the above novel PMMA material having from about 10 ppm to about 500 ppm per part of PMMA of the novel UV absorber incorporated therein. From about 100 ppm to about 250 ppm per part of PMMA is a preferred amount.

The intraocular lenses according to the present invention, may have haptics secured or affixed thereto or integral therewith and such haptics may have any of the known configurations or modifications thereof.

Both the intraocular lenses (IOLs) and the contact lenses of the present invention may be produced by any of the conventional procedures and techniques per se known in the art. See, for example, U.S. Pat. No. 4,102,567; U.S. Pat. No. 4,208,364; U.S. Pat. No. 4,158,030; U.S. Pat. No. 3,408,429; U.S. Pat. No. 3,361,858; European Patent Application No. 0 328 246; European Patent Application No. 0 333 348; Technical and Economic Effects of Contact Lens Production Methods by P. Cordrey, Optical World, 1972, Sept./Oct., pages 13 to 20; Intraocular Lens Implantation Design, E.S.P. Ford from Intraocular Lens Implantation edited by E. S. Rosen.

According to a further embodiment of the present invention, eyeglasses are produced having lens made of a polycarbonate material suitable for eyeglass lenses which has incorporated therein from about 10 ppm to about 500 ppm of the novel UV absorber per part of polycarbonate material. From about 100 ppm to about 250 ppm is a preferred amount.

For the IOLs, the contact lenses and the eyeglasses of the present invention the amount of the novel UV absorber which is incorporated can also be expressed as a weight percentage based on the weight of the PMMA or polycarbonate material. Preferably, the weight percentage of the novel UV absorber incorporated is from about 0.1% to about 5% preferably from about 0.1% to about 2%. About 0.15% by weight is a preferred amount.

Figure 1:
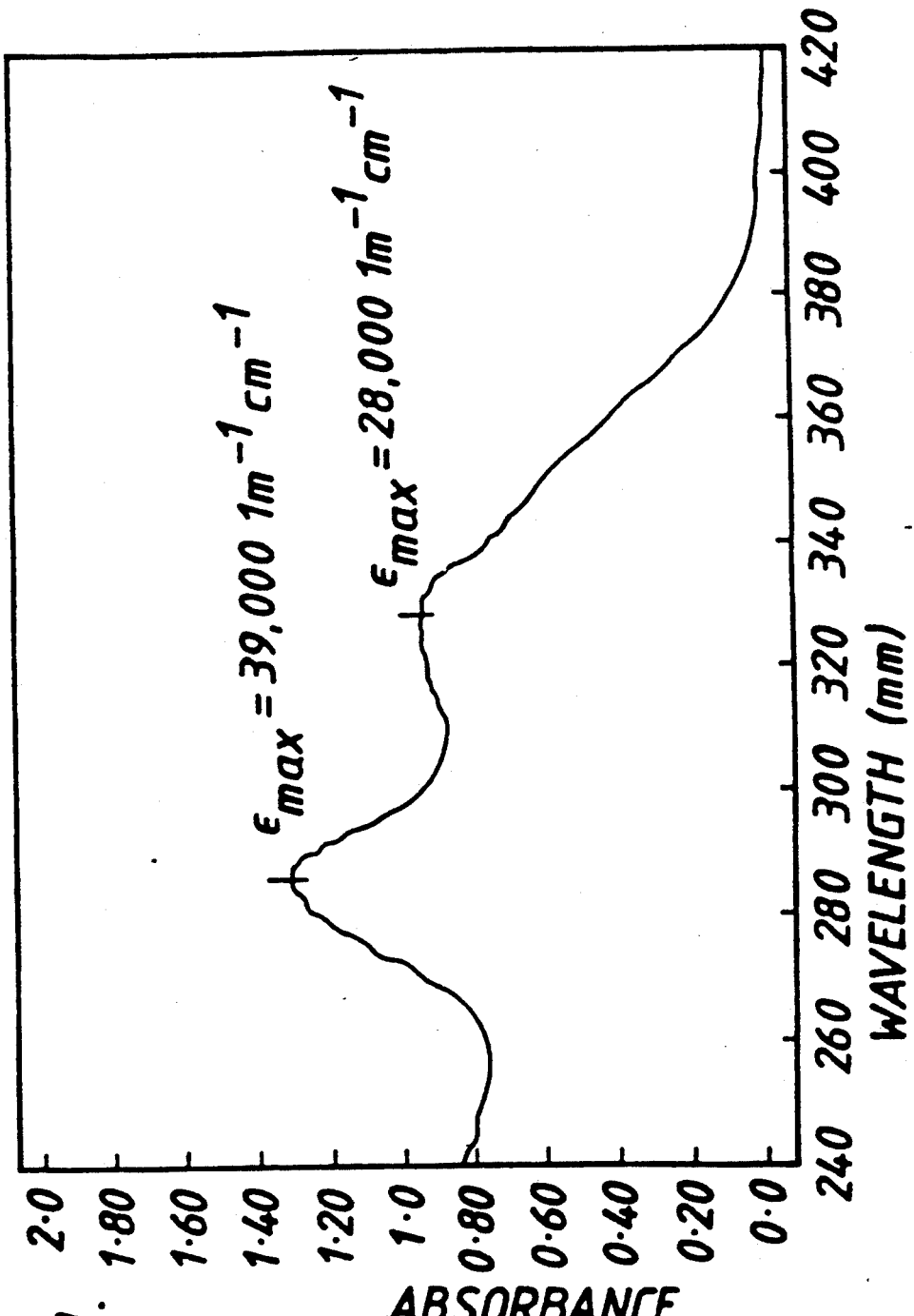
FIG. 1 shows an IR spectrum for the novel UV absorber of the present invention.
Figure 2:
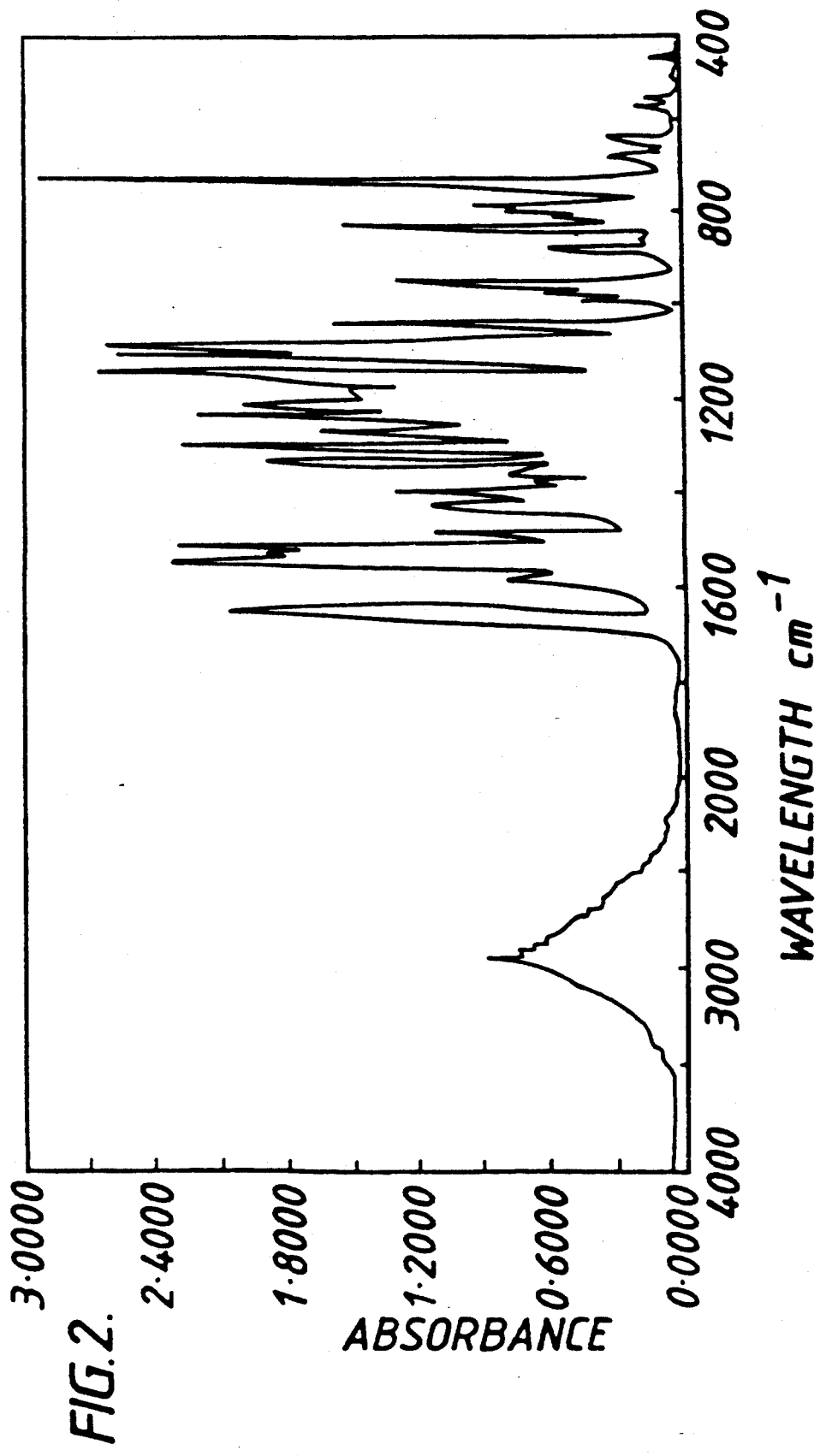
FIG. 2 shows a UV spectrum for the novel UV absorber of the present invention.

The following non-limitative Examples more particularly illustrate the production of the compound of the present invention.

EXAMPLE 1

3,5-[Di(2H-benzotriazole-2-yl)]2,4,4'-trihydroxybenzophenone

A solution of o-nitroaniline (11.1 g, 0.08M) in concentrated hydrochloric acid (30 cc) was diluted with 30 cc of water and diazotized with a solution of sodium nitrite (5.69 g, 0.08M) in water (20 cc) at 0°-5° C. The cold solution of o-nitrobenzene diazonium chloride was added over a period of one hour with stirring to a solution of 2,4,4-trihydroxybenzophenone (9.2 g, 0.04M), sodium hydroxide (7.29 g, 0.18M), and sodium bicarbonate (22 g, 0.2M) in water (300 ml) at 0°-5° C. The red diazo compound was collected, washed to neutral with water, dissolved in 170 cc aqueous sodium hydroxide (13.6 g), and reductively cyclized with Zn dust (13.6 g) at room temperature for 24 hours. Subsequently, the suspension was filtered, the residue washed with 10% aqueous NaOH; the filtrate was combined with this extract and acidified with sulfuric acid while keeping the temperature below 10° C. Precipitated crude ditriazole was collected by filtration, air-dried and extracted with ethanol to yield 9.25 g of product.

EXAMPLE 2

3,5-[Bis(2H-benzotriazole-2-vl)]2,4,dihydroxy, 4'-acryloyloxy-benzophenone

Acryloyl chloride (2 g, 0.02M) was added dropwise to a stirred solution of the ditriazole of Example 1 (4.6 g, 0.01M) in 150 cc of 0.4 molar aqueous sodium hydroxide solution at 10° C. The reaction mixture was stirred at room temperature for 30 minutes and the precipitate collected by filtration. The crude product was recrystallized from acetone-water.

| Yield 2.8 g | 90% pure by TLC |
| --- | --- |

Copolymerization of the product with methylmethacrylate was carried out at 65° C. in sealed tubes using USP-245 as an initiator.

This material has a polymerization reactivity comparable to substituted styrenes, and hence can be incorporated into a wide variety of polymers by addition copolymerization or grafting. Examples of polymers in which it can be incorporated are:

By copolymerization: polyolefins, polyacrylates, polymethacrylates, PVC, polystyrene and derivatized polystyrenes.

By grafting: polycarbonates, polyesters, polyacrylates and polymethacrylates.

A typical formulation for fabrication of IOLs is as follows: 99.7 parts per hundred (pph), methyl methacrylate (mma), 0.15 ppH BTB, 100 ppm OT-1m (mold release agent) 0.15 ppH USP 245 (which is as a free radical initiator of polymerization. This mixture is decreased by bubbling argon gas through it, placed in a glass mold, then placed in a thermostatic oven at an elevated temperature (55° C.) for 10 hours, then at 90° C. for 24 hours. After the polymerization is complete the formed sheet is post cured at 100° C. for 8 hours, then withdrawn from the oven and cooled to room temperature.

What is claimed is:

1. The compound of the formula

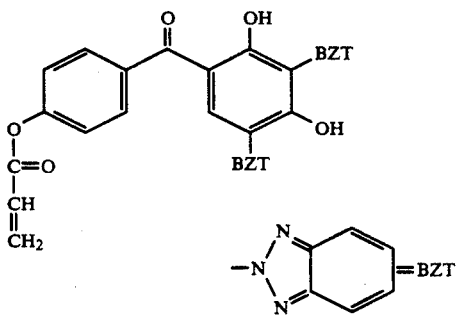

2. A PMMA material having incorporated therein, a UV absorbing amount of the compound of the formula

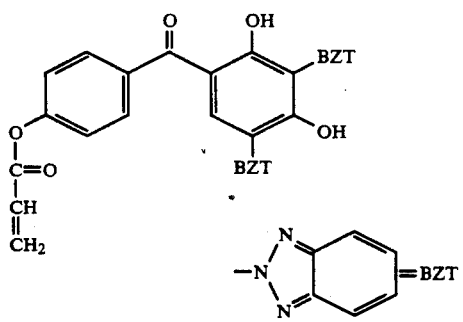

3. An intraocular lens comprising a PMMA material having incorporated therein a UV absorbing amount of the compound of the formula

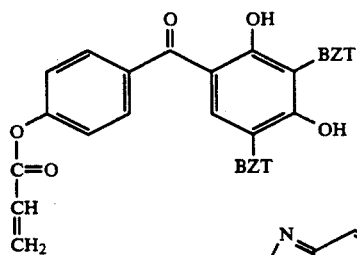
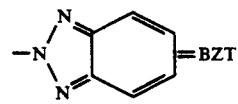

4. An intraocular lens according to claim 3 having two haptics attached thereto or integral therewith.

5. A contact lens comprising a PMMA material having incorporated therein a UV absorbing amount of the compound of the formula

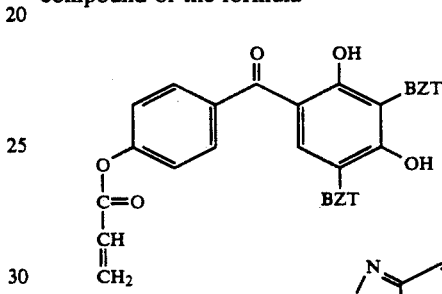
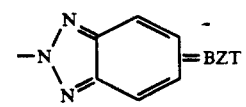

6. Eyeglasses having lenses comprising a polycarbonate material having incorporated therein, a UV absorbing amount of the compound of the formula

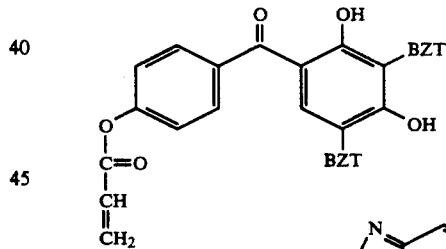
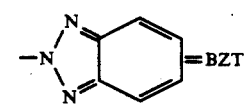

* * * * *